(12) United States Patent
Fitterer et al.

(10) Patent No.: US 11,564,710 B2
(45) Date of Patent: *Jan. 31, 2023

(54) INTRODUCER WITH EXPANDABLE CAPABILITIES

(71) Applicant: BOSTON SCIENTIFIC SCIMED, INC., Maple Grove, MN (US)

(72) Inventors: Mimi Trinh Fitterer, Belmont, CA (US); Takashi H. Ino, San Jose, CA (US); Randy S. Gamarra, Santa Clara, CA (US); Floriza Q. Escalona, San Jose, CA (US); Frederick J. Serrahsu, Fremont, CA (US); James M. Anderson, Corcoran, MN (US); Adam D. Grovender, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 131 days.

This patent is subject to a terminal disclaimer.

(21) Appl. No.: 16/730,467

(22) Filed: Dec. 30, 2019

(65) Prior Publication Data

US 2020/0146716 A1 May 14, 2020

Related U.S. Application Data

(63) Continuation of application No. 15/439,998, filed on Feb. 23, 2017, now Pat. No. 10,548,631.

(Continued)

(51) Int. Cl.
*A61B 17/34* (2006.01)
*A61M 25/06* (2006.01)
(Continued)

(52) U.S. Cl.
CPC ...... *A61B 17/3423* (2013.01); *A61B 17/3431* (2013.01); *A61B 17/3439* (2013.01);
(Continued)

(58) Field of Classification Search
CPC ............ A61B 17/3423; A61B 17/3431; A61B 17/3439; A61B 17/3468; A61B 17/3498;
(Continued)

(56) References Cited

U.S. PATENT DOCUMENTS

| 5,320,611 A | 6/1994 | Bonutti et al. |
| 5,863,284 A | 1/1999 | Klein |

(Continued)

FOREIGN PATENT DOCUMENTS

| JP | 09050594 A | 2/1997 |
| JP | 2007054646 A | 3/2007 |

(Continued)

OTHER PUBLICATIONS

European Search Report Application No. 20190606.2-1113 dated Oct. 21, 2020.

(Continued)

*Primary Examiner* — Ryan J. Severson
(74) *Attorney, Agent, or Firm* — Seager, Tufte & Wickhem LLP (57) ABSTRACT

An example introducer is disclosed. An example introducer includes an inner liner including a lumen, a distal region and at least one folded portion extending along the distal region. The introducer also includes a reinforcing member having a length and including at least one spine extending along the length of the reinforcing member. The introducer also includes a sheath disposed along at least a portion of the introducer, wherein the sheath includes at least one perforation, wherein material adjacent to the at least one folded portion is removed from a distal portion of the introducer to form a tip region. The introducer also includes a tip member disposed along the tip region.

1 Claim, 10 Drawing Sheets

Related U.S. Application Data (60) Provisional application No. 62/303,774, filed on Mar. 4, 2016.

(51) Int. Cl.
*A61M 25/00* (2006.01)
*A61B 90/00* (2016.01)

(52) U.S. Cl.
CPC ..... *A61B 17/3498* (2013.01); *A61M 25/0012* (2013.01); *A61M 25/0023* (2013.01); *A61M 25/0668* (2013.01); *A61B 2017/3454* (2013.01); *A61B 2090/3966* (2016.02); *A61M 25/0051* (2013.01); *A61M 25/0662* (2013.01); *A61M 2025/006* (2013.01); *A61M 2025/0024* (2013.01)

(58) Field of Classification Search
CPC ... A61B 2017/3445; A61B 2017/3454; A61M 25/0023; A61M 25/0051; A61M 25/0662; A61M 2025/0024
See application file for complete search history.

(56) References Cited

U.S. PATENT DOCUMENTS

| | | | |
|---|---|---|---|
| 5,997,508 | A | 12/1999 | Lunn et al. |
| 6,080,141 | A | 6/2000 | Castro et al. |
| 6,090,072 | A | 7/2000 | Kratoska et al. |
| 6,197,016 | B1 | 3/2001 | Fourkas et al. |
| 6,652,492 | B1 | 11/2003 | Bell et al. |
| 7,144,386 | B2 | 12/2006 | Korkor et al. |
| 7,329,268 | B2 | 2/2008 | Van Nguyen et al. |
| 7,713,193 | B2 | 5/2010 | Nance et al. |
| 7,762,995 | B2 | 7/2010 | Eversull et al. |
| 7,766,820 | B2 | 8/2010 | Core |
| 7,780,692 | B2 | 8/2010 | Nance et al. |
| 7,837,692 | B2 | 11/2010 | Mulholland et al. |
| 8,090,936 | B2 | 1/2012 | Fallon et al. |
| 8,092,481 | B2 | 1/2012 | Nance et al. |
| 8,690,936 | B2 | 4/2014 | Nguyen et al. |
| 8,790,387 | B2 | 7/2014 | Nguyen et al. |
| 9,044,577 | B2 | 6/2015 | Bishop et al. |
| 9,241,735 | B2 | 1/2016 | Kick et al. |
| 9,301,840 | B2 | 4/2016 | Nguyen et al. |
| 9,301,841 | B2 | 4/2016 | Nguyen et al. |
| 9,320,508 | B2 | 4/2016 | Carroux |
| 9,415,186 | B2 | 8/2016 | Chebator et al. |
| 9,801,657 | B2 | 10/2017 | Furnish et al. |
| 9,956,376 | B2 | 5/2018 | Anderson et al. |
| 2003/0233115 | A1* | 12/2003 | Eversull ............ A61M 25/1002 606/194 |
| 2004/0006344 | A1 | 1/2004 | Nguyen et al. |
| 2004/0087968 | A1 | 5/2004 | Core |
| 2005/0124937 | A1 | 6/2005 | Kick et al. |
| 2005/0125021 | A1 | 6/2005 | Nance et al. |
| 2006/0135981 | A1 | 6/2006 | Lenker et al. |
| 2007/0021768 | A1 | 1/2007 | Nance et al. |
| 2008/0004521 | A1 | 1/2008 | Hundley et al. |
| 2008/0004571 | A1 | 1/2008 | Voss |
| 2009/0221965 | A1 | 9/2009 | Osypka |
| 2010/0082000 | A1 | 4/2010 | Honeck et al. |
| 2010/0198160 | A1 | 8/2010 | Voss |
| 2012/0323180 | A1 | 12/2012 | Chebator et al. |
| 2014/0236122 | A1 | 8/2014 | Anderson et al. |
| 2015/0238178 | A1 | 8/2015 | Carroux |
| 2016/0074067 | A1 | 3/2016 | Furnish et al. |
| 2016/0213882 | A1 | 7/2016 | Fitterer et al. |
| 2017/0252062 | A1 | 9/2017 | Fitterer et al. |
| 2018/0161064 | A1 | 6/2018 | Fitterer et al. |
| 2018/0199960 | A1 | 7/2018 | Anderson et al. |
| 2018/0221149 | A1 | 8/2018 | Reynolds et al. |
| 2018/0325548 | A1 | 11/2018 | Haverkost et al. |
| 2018/0325549 | A1 | 11/2018 | Thoreson et al. |
| 2019/0029825 | A1 | 1/2019 | Fitterer et al. |

FOREIGN PATENT DOCUMENTS

| | | |
|---|---|---|
| JP | 2010530792 A | 9/2010 |
| JP | 2013116220 A | 6/2013 |

OTHER PUBLICATIONS

International Search Report and Written Opinion dated May 15, 2017 for International Application No. PCT/US2017/020010.

* cited by examiner

INTRODUCER WITH EXPANDABLE CAPABILITIES

RELATED APPLICATIONS

This application claims priority to U.S. application Ser. No. 15/439,998, filed Feb. 23, 2017, now U.S. Pat. No. 10,548,631, and U.S. Provisional Application Ser. No. 62/303,774, filed Mar. 4, 2016.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough).

SUMMARY

This disclosure provides design, material, manufacturing method, and use alternatives for medical devices. An example introducer includes an inner liner including a lumen, a distal region and at least one folded portion extending along the distal region. The introducer also includes a reinforcing member having a length and including at least one spine extending along the length of the reinforcing member. The introducer also includes a sheath disposed along at least a portion of the introducer, wherein the sheath includes at least one perforation, wherein material adjacent to the at least one folded portion is removed from a distal portion of the introducer to form a tip region. The introducer also includes a tip member disposed along the tip region.

Alternatively or additionally to any of the examples above, wherein the at least one folded portion allows the liner to radially expand.

Alternatively or additionally to any of the examples above, wherein the folded portions wrap along an inner surface of the inner liner.

Alternatively or additionally to any of the examples above, wherein the at least one spine of the reinforcing member has a substantially constant width along the length the reinforcing member.

Alternatively or additionally to any of the examples above, wherein the at least one spine of the reinforcing member includes a proximal end, a distal end and a width, wherein the width of the spine varies from the distal end of the spine to the proximal end of the spine.

Alternatively or additionally to any of the examples above, wherein the at least one spine of the reinforcing member includes a thickness, wherein the thickness of the spine varies along the length of the reinforcing member.

Alternatively or additionally to any of the examples above, wherein the at least one perforation of the sheath includes an opening, and wherein the opening is configured to tear apart as the at least one folded portion radially expands.

Alternatively or additionally to any of the examples above, wherein the sheath includes a length and a plurality of perforations, and wherein the plurality of perforations are longitudinally aligned along the length of the sheath.

Alternatively or additionally to any of the examples above, wherein the sheath further includes a proximal end, a distal end and a length extending therebetween, and wherein each of plurality of perforations are separated by a distance, and wherein the distance between each of the plurality of perforations varies along the length of the sheath from the distal end to the proximal end.

Alternatively or additionally to any of the examples above, wherein each of the perforations define a surface area, and wherein the surface area of each of the perforations varies along the length of the sheath from the distal end to the proximal end.

Alternatively or additionally to any of the examples above, wherein the at least one perforation is substantially radially aligned with the at least one folded portion.

Alternatively or additionally to any of the examples above, wherein the tip member is designed to tear as the at least one folded portion radially expands.

Alternatively or additionally to any of the examples above, wherein the tip member is radiopaque.

Alternatively or additionally to any of the examples above, wherein the tip member includes a tapered portion.

Alternatively or additionally to any of the examples above, wherein the at least one spine is substantially radially aligned with the at least one folded portion.

Another example introducer comprises:

an inner liner including a lumen, a distal region and a plurality of folds disposed along an inner surface of the liner;

a spine member having a length and a plurality of longitudinally extending support members;

a sheath disposed along at least a portion of the liner, wherein the sheath includes a plurality of openings extending at least partially through the sheath;

wherein material adjacent to the plurality of folds is removed from a distal portion of the introducer to form a tip region; and a tip member disposed along the tip region.

Alternatively or additionally to any of the examples above, wherein the plurality of folds are configured to radially expand.

Alternatively or additionally to any of the examples above, wherein each of the plurality of reinforcing members includes a proximal end, a distal end and a width, wherein the width of each of the reinforcing members decreases from the distal end of the reinforcing member to the proximal end of the reinforcing member.

Alternatively or additionally to any of the examples above, wherein the plurality of openings on the sheath are configured to tear apart as the plurality of folds radially expand.

Alternatively or additionally to any of the examples above, wherein the sheath further includes a proximal end, a distal end and a length extending therebetween, and wherein each of plurality of openings are separated by a distance, and wherein the distance between each of the plurality of openings increases along the length of the sheath from the distal end to the proximal end.

Alternatively or additionally to any of the examples above, wherein each of the openings define a surface area, and wherein the surface area of each of the openings decreases along the length of the sheath from the distal end to the proximal end.

Another example introducer comprises:

an inner liner including a lumen, a distal region and a plurality of folds extending along an inner surface of the liner, the inner liner including a first configuration and an expanded configuration;

a spine member including at least one reinforcing member;

a sheath disposed along at least a portion of the liner, wherein the sheath includes at least one opening extending at least partially through the sheath;

wherein material adjacent to the at least one folded portion is removed from a distal portion of the introducer to form a tip region; and a tip member disposed along the tip region;

wherein the folds along an expandable region are configured to shift between a first configuration and an expanded configuration.

The above summary of some examples is not intended to describe each disclosed embodiment or every implementation of the present disclosure. The Figures, and Detailed Description, which follow, more particularly exemplify these examples.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough). The following examples disclose an intravascular medical device including an expandable introducer, whereby the introducer is designed to expand from a reduced profile, unexpanded configuration to an expanded configuration.

Figure 1:
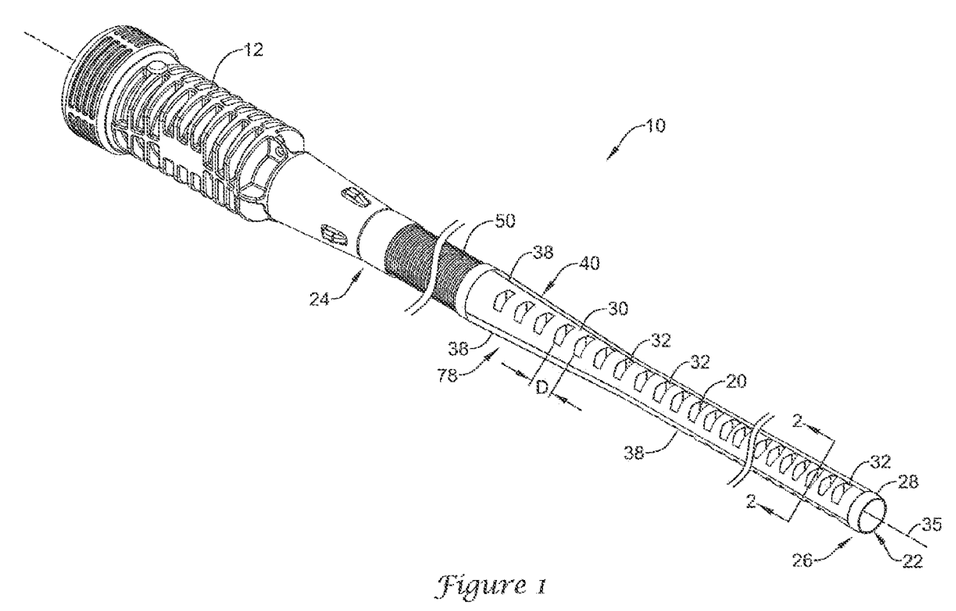
FIG. 1 is a perspective view of an example introducer.

FIG. 1 illustrates an example expandable introducer (e.g., delivery sheath, access sheath, etc.) 10 including an elongated compliant liner (e.g., tubular membrane, etc.) 20 having a lumen 22, proximal portion 24 and a distal portion 26. The introducer 10 may also include an outer sheath 30 and a spine member 40. Spine member 40 may include reinforcement members 38.

Introducer 10 may include a tapered region 78. In some examples, the tapered region 78 may be positioned proximal to the distal portion 26 of introducer 10. In some examples at least a portion of distal portion 26 of introducer 10 may have a substantially constant outer diameter which transitions into tapered portion 78. At least a portion of tapered portion 78 may have an outer diameter which is greater than the outer diameter of at least a portion of distal region 26. However, this is not intended to be limiting. It is contemplated that any portion of the introducer 10 may include any number of tapers, constant diameter regions or combinations thereof.

The proximal portion 24 of the liner 20 and/or sheath 30 may be attached to a spring member 50. In some examples, liner 20 and/or sheath 30 may cover either the outer surface, inner surface or both the inner and outer surfaces of spring member 50. For example, in some instances, spring member 50 may be positioned between (e.g., laminated) liner 20 and/or sheath 30.

Additionally, in some instances the spring member 50, sheath 30 and/or liner (e.g., a combination of spring member 50, sheath 30 and liner 20) may be attached to a hub 12. The hub 12 may include a hemostatic valve or seal disposed therein. The hemostatic valve or seal may prevent blood or other bodily fluid(s) from flowing proximally through the lumen 22 of liner 20. In at least some examples, the hub 12 may include a port in fluid communication with the lumen 22 of liner 20.

FIG. 1 illustrates an outer sheath (e.g., perforated covering) 30 and a spine member (e.g., support member) 40 fixedly attached to liner 20. As will be described in greater detail below, both outer sheath 30 and spine 40 may be disposed (e.g., attached) along liner 20 from distal portion 26 to proximal portion 24. Outer sheath 30 may include one or more apertures (e.g., openings) 32 extending through at least a portion of the wall thickness of sheath 30. As shown in FIG. 1, the one or more apertures 32 may be aligned with one another along the central longitudinal axis 35 of introducer 10. Additionally, apertures 32 may be positioned between adjacent reinforcement members 38. For example, FIG. 1 shows apertures 32 positioned between two reinforcement members 38. As will be described in greater detail below, the distal portion 26 of introducer 10 may include an atraumatic tip member 28.

Figure 2:
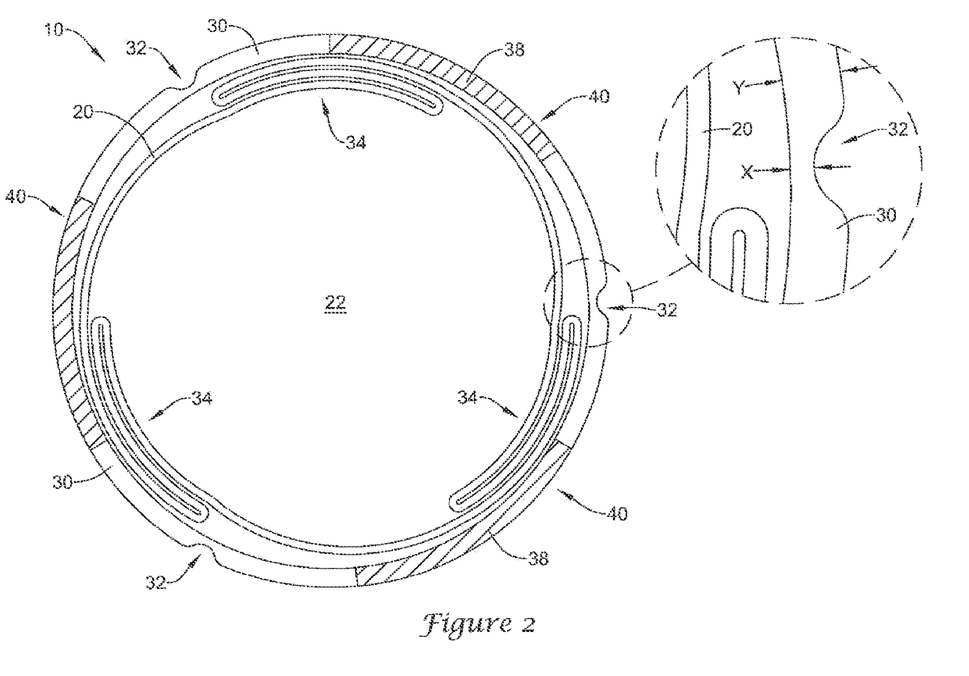
FIG. 2 is a cross-sectional view of an example introducer taken along the line 2-2 of FIG. 1.

FIG. 2 shows a cross-sectional view along line 2-2 of FIG. 1. FIG. 2 illustrates liner 20 including three folded sections 34 extending along the inner surface of liner 20. While FIG. 2 shows three folded sections 34, it is contemplated that liner 20 may include greater or less than three folded sections 34. For example, liner 20 may include 1, 2, 4, 5, 6, 7, 8, 9, 10 or more folded sections 34.

Additionally, it can be appreciated that FIG. 2 represents the cross-section of introducer 10 after manufacturing. For example, FIG. 2 illustrates that spine 40 is incorporated into the tubular wall of outer sheath 30. In other words, FIG. 2 illustrates that in some examples, outer sheath 30 and spine member 40 may be manufactured (e.g., melted/reflowed together) such that they form a unitary member. Similarly to that discussed with respect to folded members 34, it can be appreciated that while FIG. 2 shows spine member 40 including three support members 38, spine 40 may include greater or less than three support members 38. For example, spine 40 may include 1, 2, 3, 4, 5, 6, 7, 8, 9, 10 or more support members 38.

As discussed above, in some instances outer sheath 30 may include one or more apertures 32 extending at least partially through the wall thickness of outer sheath 30. The detailed view in FIG. 2 shows one example of an aperture 32 having extending partially through the tubular wall of outer sheath 30. The reduced wall thickness of aperture 32 is depicted as thickness "X." Further, a portion of the tubular wall of outer sheath 30 adjacent to aperture 32 is depicted as "Y." It can be seen that the thickness "X" of aperture 32 is less than the thickness "Y." As will be described in greater detail below, it can be appreciated that the reduced wall thickness "X" (as compared to wall thickness "Y") may create a preferential "tear point" within outer sheath 30. In other words, aperture(s) 32 may define a perforated tear line extending along introducer 10.

Additionally, in at least some examples, the apertures 32 (e.g., openings, cutouts, perforations, notches, holes) or other weakening features formed in the wall of the sheath 30 may be positioned adjacent to, radially outward of, in communication with, and/or directly over the one or more folds 34 formed in liner 20. For example, FIG. 2 shows apertures 32 positioned directly over the one or more folds 34 in liner 20. More particularly, in some instances apertures 32 may be aligned at a point along outer sheath 30 in which fold 34 begins to wrap underneath outer sheath 30. It can be appreciated that the point at which aperture 32 is aligned with fold 34 may be the point at which fold 34 initially begins to separate when liner 20 shifts from the configuration shown in FIG. 2 to an expanded configuration.

Figure 3:
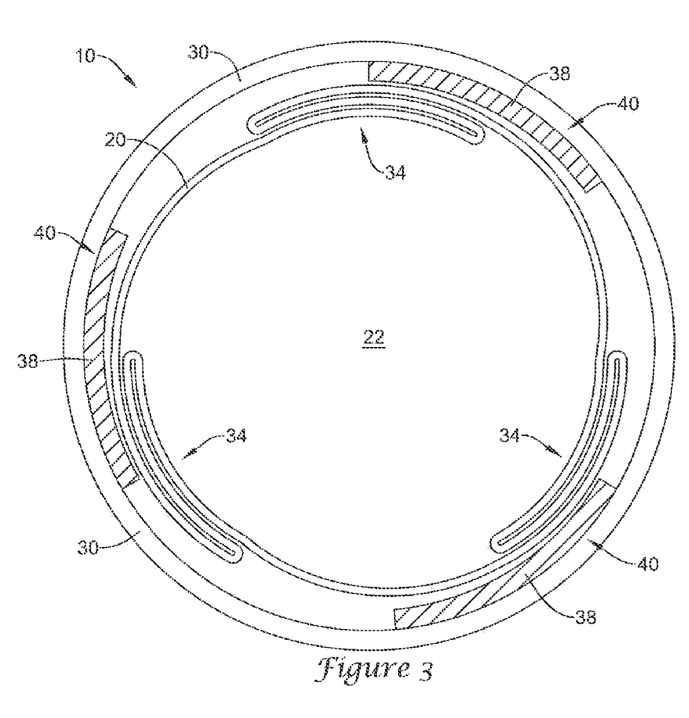
FIG. 3 is a cross-sectional view of an example introducer.

One example methodology to construct the introducer 10 (shown in FIG. 1) may include configuring spine 40, outer sheath 30 and liner 20 as shown in FIG. 3 followed by applying heat such that outer sheath member melts (e.g., reflows) and encapsulates spine member 40 as shown in FIG. 2. It can be appreciated that liner 20 may be constructed from a material that has a higher melting point than either outer sheath 30 or spine member 40, and therefore, will not melt upon the application of heat sufficient to melt outer sheath 30 and/or spine member 40 together. In other examples, liner 20 may be constructed from a non-thermoplastic material designed to resist melting while heat is applied to reflow outer sheath 30 and spine 40 together. Additionally, it is contemplated that arrangement of liner 20, outer sheath 30 and spine member 40 may include a variety of configurations throughout the manufacturing steps. For example, examples contemplated herein may include different positions, alignment, spacing, sizes, dimensions, etc. of spine 40, liner 20 and/or sheath 30 relative to one another during the manufacturing process and/or final design.

Figure 4:
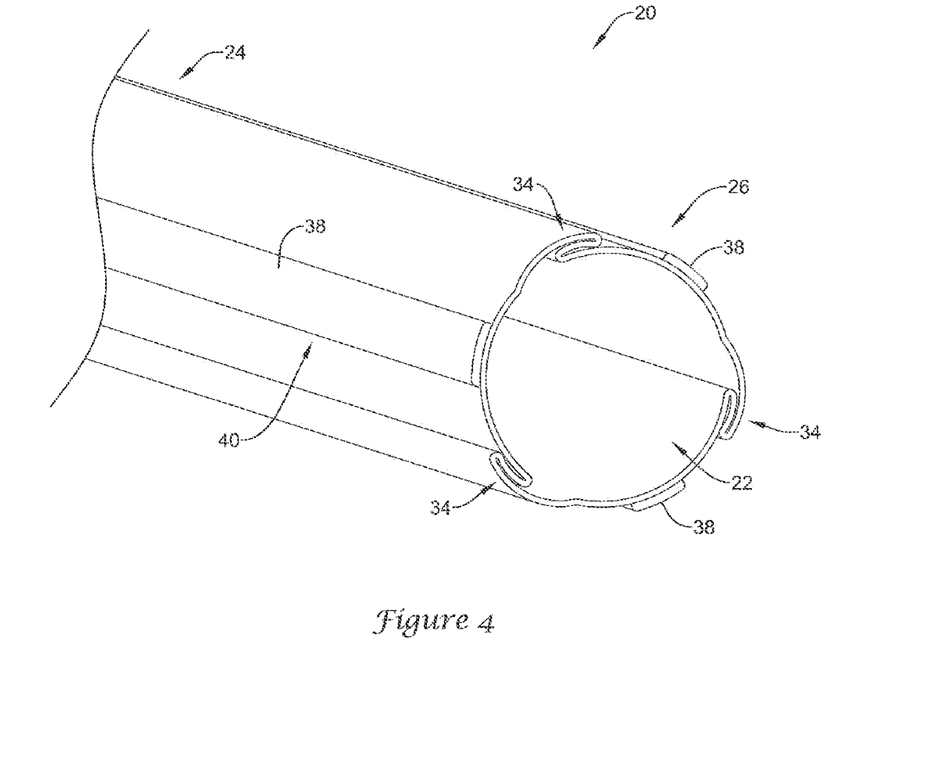
FIG. 4 is a perspective view of an example liner.

FIG. 4 shows liner 20 having a substantially annular shape and a lumen 22 extending at least partially therethrough. In some examples, the lumen 22 may extend from a proximal end 24 of liner 20 to a distal end 26 of liner 20. Additionally, the lumen 22 may extend completely through an entire length of liner 20. It is contemplated that other shapes and/or configurations are possible within the scope of the present disclosure, as will be apparent from the discussion below, and other shapes or configurations discussed herein may be used in the configuration(s) schematically shown in the figures.

As stated, liner 20 may be described as having a compliant elongated tubular structure having a lumen 22 extending therethrough from proximal end 24 to a distal end 26. Liner 20 may include a wall having an inner surface and an outer surface. In some examples, a thickness of the wall may be defined by the inner surface and the outer surface.

In some examples, liner 20 and/or lumen 22 may be configured to radially expand from a delivery configuration to an expanded configuration when subjected to a radially outward force from within the lumen 22 and/or liner 20. In at least some examples, liner 20 may be substantially or completely compliant and/or liner 20 may have no radial self-bias—that is, no radially inward self-bias and/or no radially outward self-bias. In other words, liner 20 may be non-self-supporting and may not include a mechanism to radially expand and/or open on its own (i.e., absent a radially outward force exerted upon liner 20). Instead, liner 20 may require a device or object that has a greater outer diameter than an inner diameter of lumen 22 and/or liner 20 to be disposed within lumen 22 to push and/or force liner 20 radially outward toward the expanded configuration.

Additionally, liner 20 may not require a radially inward force be applied upon itself to collapse itself inward when there is no device, object, etc. disposed within lumen 22. In other words, liner 20 may not be held open or maintain a particular expanded size on its own, or liner 20 may be non-self-supporting as mentioned above. Similarly, liner 20 may not be biased to collapse inwardly on its own. In other words, liner 20 may take the shape and/or form of surrounding tissue(s) after being expanded. For example, a constriction in or of a vessel or body lumen in which liner 20 is disposed may urge liner 20 radially inward, but liner 20 is not self-biased inwardly on its own (i.e., liner 20 may have zero return force after expanding/opening).

In the delivery configuration, lumen 22 may have a first inner diameter defined by the inner surface of the wall of liner 20. In some examples, as will be apparent herein, the first inner diameter may be defined as a first inner radial extent and/or distance from a central longitudinal axis 35 of liner 20 and/or the expandable introducer 10. In the expanded configuration, lumen 22 may have a second inner diameter defined by the inner surface of the wall. In some examples, as will be apparent herein, the second inner diameter may instead be defined as a second inner radial extent and/or distance from a central longitudinal axis 35 of liner 20 and/or the expandable introducer 10. In some examples, the second inner diameter may be greater than the first inner diameter. Similarly, the second inner radial extent may be greater than the first inner radial extent.

Similarly, liner 20 may have an outer diameter and/or outer radial extent defined by the outer surface of the wall of liner 20. In the delivery configuration, liner 20 may have a first outer diameter and/or first outer radial extent defined by the outer surface of the wall. In the expanded configuration, liner 20 may have a second outer diameter and/or a second outer radial extent defined by the outer surface of the wall. In some examples, the second outer diameter may be greater than the first outer diameter. Similarly, the second outer radial extent may be greater than the first outer radial extent.

As discussed above, liner 20 may include one or more folds 34 formed therein in the delivery configuration. In some examples, the one or more folds 34 may include two folds, three folds, four folds, five folds, six folds, seven folds, eight folds, nine folds, ten folds, or another desirable number or quantity of folds. In at least some examples, liner 20 may be disposed radially inward of outer sheath 30. In some examples, the one or more folds 34 may each fold back on themselves to form, for example, a wave shape, an S-shape, T-shape and/or a Z-shape when viewed in cross-section. In some examples, each of the one or more folds forming a T-shape may include two or more distinct waves, S-shaped, or Z-shaped secondary folds within and thus forming each of the one or more T-shaped folds. Other shapes and configurations, while not expressly illustrated, are also contemplated.

Additionally, in some examples, liner 20 may be configured to permit the lumen 22 to radially expand from the first inner diameter and/or the first inner radial extent to the second inner diameter and/or the second inner radial extent. In some examples, liner 20 is configured to substantially prevent axial stretching along the lumen 22. In other words, liner 20 may permit the lumen 22 to expand radially outward from a central longitudinal axis 35 of liner 20 and/or the expandable introducer 10 without stretching or expanding in an axial or longitudinal direction. In some examples, the second inner diameter and/or the second inner radial extent may be greater than the first outer diameter and/or the first outer radial extent. Because liner 20 may be made from an inelastic material, it may be configured to expand radially outward to a predetermined maximum second inner diameter and/or second inner radial extent, but may not stretch or expand radially outward beyond the predetermined maximum second inner diameter and/or second inner radial extent.

In some examples, the inner surface of the wall of liner 20 may include one or more layers or coatings, such as a lubricious coating, a hydrophilic coating, a hydrophobic coating, or other suitable coatings, and the like, or liner 20 may include a lubricant disposed within the lumen 22. In some examples, an outer surface of the expandable introducer 10 and/or outer sheath 30 may include one or more layers or coatings, such as a lubricious coating, a hydrophilic coating, a hydrophobic coating, or other suitable coating, and the like, or the expandable introducer 10 and/or outer sheath 30 may include a lubricant disposed upon the outer surface thereof.

Additionally, FIG. 4 shows spine member 40 positioned along th outer surface of liner 20. Spine member 40 may have one or more reinforcement member 38 extending along an outer surface of liner 20. In some instances, spine member 40 may be positioned (e.g., attached, glued, tacked, adhered, etc.) to the outer surface of liner 20 during the manufacturing process. For example, in some examples spine member 40 may be positioned on the outer surface of liner 20 prior to outer sheath 30 being positioned over the combination of liner 20 and outer sheath 30.

Figure 5:
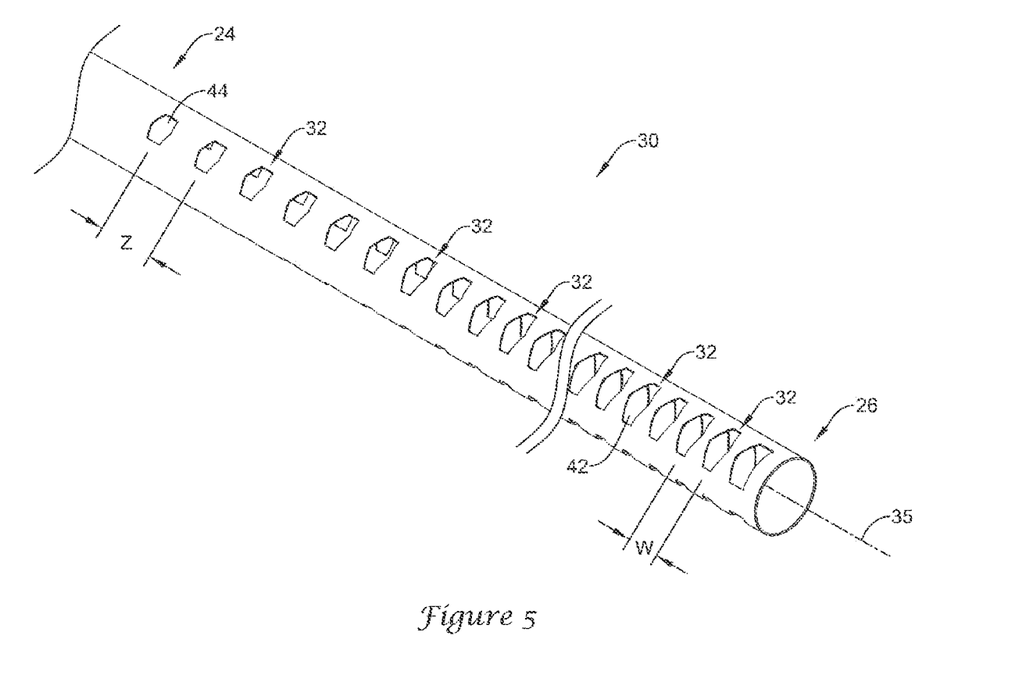
FIG. 5 is a perspective view of an example outer sheath.

FIG. 5 shows an example outer sheath 30. In some examples, outer sheath 30 may be fixedly attached to the outer surface of liner 20 and/or spine 40. In some examples, outer sheath 30 may be bonded, laminated, fused, glued, co-molded, melted, welded, or other suitable means, to liner 20 and/or spine 40. In other words, in some examples, outer sheath 30 may be permanently attached to the outer surface of liner 20.

In some examples, outer sheath 30 may be formed from a polymeric material, which may form at least a portion of a wall of outer sheath 30. In some examples, outer sheath 30 may be formed from the same material as liner 20. In some examples, outer sheath 30 may be formed from a different material than liner 20. In some examples, some or all of outer sheath 30 may be fixedly attached to the outer surface of the wall of liner 20. In some examples, the entire outer sheath 30 may be fixedly attached to the outer surface of the wall of liner 20 and/or spine 40.

In some examples, at least a portion of outer sheath 30 may extend continuously around a circumference of liner 20 in a first configuration. In some examples, at least a portion of outer sheath 30 may be discontinuous. In other words, and as described above, in some examples outer sheath 30 may include a plurality of apertures 32 (e.g., openings, cutouts, perforations, notches, holes, apertures, or other weakening features) formed in the wall of outer sheath 30 which effectively remove at least (or in some cases, only) a portion of the wall of outer sheath 30. While apertures 32 shown in FIG. 5 are substantially hexagonal, it is contemplated that apertures 32 may be any shape. For example, apertures 32 may be circular, square, rectangular, ovular, triangular, diamond shaped, or the like.

In some examples, the plurality of apertures 32 formed in the wall of outer sheath 30 may be arranged in one or more longitudinal lines along the length of the expandable introducer 10, liner 20, and/or outer sheath 30. In some examples, the plurality of apertures 32, or other weakening features formed in the wall of outer sheath 30 may extend laterally and/or transversely through the wall of outer sheath 30 relative to the central longitudinal axis 35. In some examples, a wall thickness of the outer sheath may be tapered about the circumference of liner 20 such that a reduced thickness region of outer sheath 30 is disposed adjacent to, radially outward of, in communication with, and/or directly over the one or more folds 34 of liner 20.

Further, in some examples the apertures 32 included in outer sheath 30 may be spaced apart from one another. For example, FIG. 5 shows adjacent apertures 32 located near the distal end 26 of outer sheath 30 spaced apart from one another a distance "W". Similarly, FIG. 5 shows two other adjacent apertures 32 located near the proximal end 24 of outer sheath 30 spaced apart from one another a distance "Z". It can be appreciated that in some examples, distance "W" and distance "Z" may be equal. In other words, in some examples all the apertures 32 positioned along outer sheath 30 may be spaced equidistant from one another. However, in other examples, it can be appreciated that distances "W" and "Z" may be different. In other words, in some examples apertures 32 may include variable spacing between one another. For example, it can be appreciated that the spacing between apertures 32 may gradually increase from the distal portion 26 to the proximal portion 24 of outer sheath 30.

Similarly, FIG. 5 illustrates the apertures 32 having a surface area. While the term surface area may be used to herein, the "surface area," of a given aperture 32 as described herein may be defined as the "area" bounded by the shape of a given aperture 32. For example, in FIG. 5, the surface area of a given aperture 32 may be defined as the area bounded by an individual hexagon. Further, FIG. 5 shows two different individual apertures 42 and 44. Aperture 42 may be positioned near the distal end 26 of outer sheath 30 while aperture 44 may be positioned near the proximal end 24 of outer sheath 30. In some examples, the surface area of the apertures 32 of outer sheath 30 may be equal. In other examples, such as that shown in FIG. 5, the surface area of apertures 32 may be different. For example, the surface area of aperture 42 may be larger than that of aperture 44. Further, the area of apertures 32 may decrease along outer sheath 30 from the distal portion 26 to the proximal portion 24. Additionally, during the manufacturing process, it is contemplated that the size, shape and/or spacing between apertures 32 may change. For example, smaller apertures (e.g., aperture 44) may expand as the proximal portion 24 of the outer sheath 30 may be pulled and/or stretched over the tapered portion 78 of introducer 10, for example. It is further contemplated that various different arrangements, spacing, areas, surface areas and/or alignments of apertures 32 may be utilized in the design of outer sheath 30.

Additionally, as described above with respect to FIG. 2, it can be appreciated that outer sheath 30 may include a given wall thickness at various locations along its length. It can further be appreciated that the wall thickness of outer sheath 30 may vary along its length. For example, while some examples contemplated herein may include apertures 32 being defined as "holes" through the wall of outer sheath 30, in other examples, apertures 32 may be defined as substantially "thinner" sections of the wall of outer sheath 30.

In some examples, outer sheath 30 may be configured to separate, split, or tear as liner 20 is expanded from a first configuration to a second, expanded configuration. The expansion may be due to a radially outward force applied from within liner 20. In some examples, outer sheath 30 may be configured to separate, split, perforate and/or tear along and/or through the plurality of apertures 32, or other weakening features formed in the wall of outer sheath 30. In other words, outer sheath 30 may separate, split, or tear where outer sheath 30 is discontinuous and/or constructed of a thinner material. In other words, as liner 20 radially expands outward toward an expanded configuration, outer sheath 30 may tear along preferential tear points corresponding to apertures 32. Further, the expansion of sheath 30 may correlate with the expansion of the lumen 22. Lumen 22 may expand from a first inner diameter and/or the first inner radial extent to a second inner diameter and/or a second inner radial extent.

As discussed above, the plurality of apertures 32, or other weakening features formed in the wall of outer sheath 30 may be positioned adjacent to, radially outward of, in communication with, and/or directly over the one or more folds 34 formed in liner 20. As mentioned above, in some examples, the plurality of apertures 32, or other weakening features formed in the wall of outer sheath 30 may be arranged in one or more longitudinal lines along the length of the expandable introducer 10, liner 20 and/or outer sheath 30. Accordingly, in some examples, the plurality of apertures 32 or other weakening features formed in the wall of outer sheath 30 may be arranged in one or more longitudinal lines adjacent to, radially outward of, in communication with, and/or directly over the one or more folds 34 and/or the two or more secondary folds formed in liner 20. In some examples, the one or more longitudinal lines may directly correspond to the one or more folds 34 and/or the two or more secondary folds. In some examples, there may be more longitudinal lines than folds and/or secondary folds (i.e., 2 folds with 3 or more lines of openings, cutouts, etc., 3 folds with 4 or more lines of openings, cutouts, etc.). In some examples, the reduced thickness region and/or a substantially thinner thickness of outer sheath 30 may be disposed adjacent to, radially outward of, in communication with, and/or directly over the one or more folds 34 and/or the two or more secondary folds of liner 20.

Figure 6:
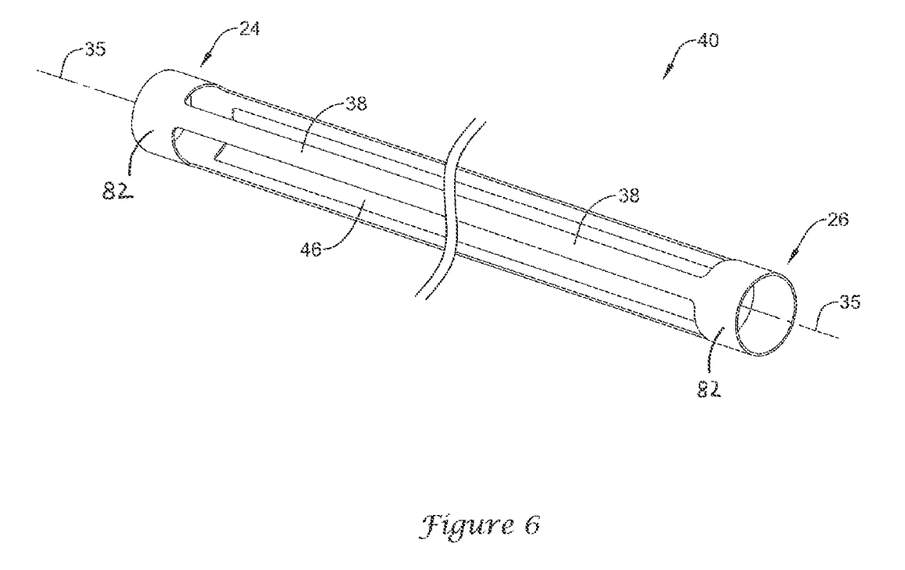
FIG. 6 is a perspective view of an example spine member.

FIG. 6 is a perspective view of an example spine member 40 including reinforcement members 38 extending from a distal end 26 of spine 40 to a proximal end 24 of spine 40. FIG. 6 shows spine member 40 member having an openings 46 defined between adjacent reinforcement members 38. While FIG. 6 shows spine member 40 having three reinforcement members 38, it is contemplated that spine member 40 may have less than or greater than three reinforcement members 38. For example, spine member 40 may have 1, 2, 3, 4, 5, 6, 7, 8, 9, 10 or more reinforcement members 38. Further, FIG. 6 shows that in some examples, the width of reinforcement members 38 may be substantially uniform. In other words, the width of reinforcement members 38 may remain substantially uniform along spine member 40 from proximal end 24 to distal end 26. Additionally, FIG. 6 shows reinforcement members 38 spaced substantially equidistant around longitudinal axis 34. However, it is further contemplated that reinforcement members 38 may be spaced at variable distances around longitudinal axis 34.

Figure 7:
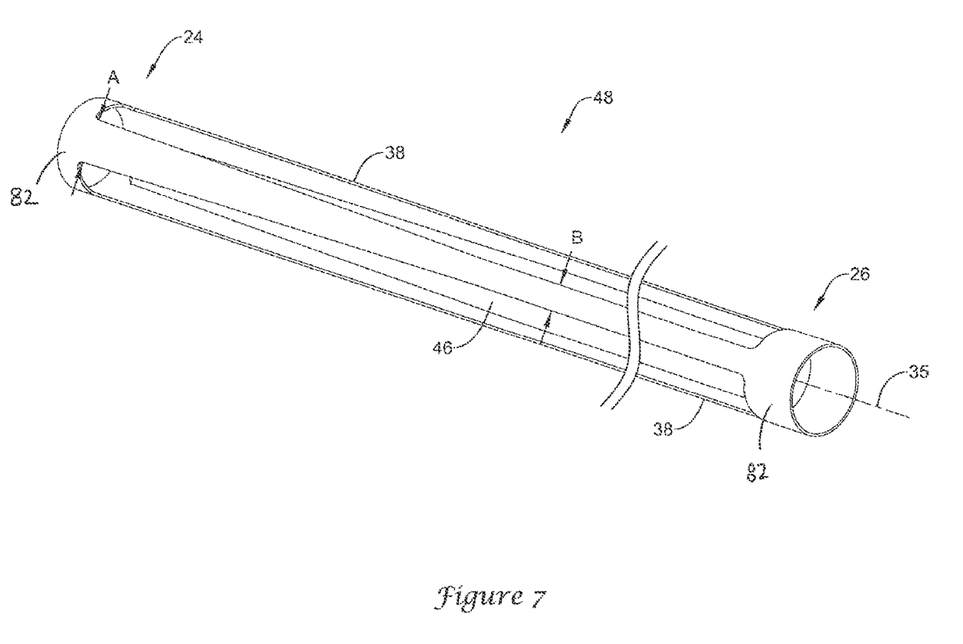
FIG. 7 is a perspective view of an example spine member.

FIG. 7 illustrates another example spine member 48. The spine member 48 of FIG. 7 may be similar to the spine member 40 shown in FIG. 7. However, the spine member 48 of FIG. 7 may include one or more reinforcement members 38 having a variable width along the length of spine member 48. For example, FIG. 7 shows an example reinforcement member 38 having a width "A" at one location and a different width "B" at a different location. As shown in FIG. 7, in some examples width "B" may be substantially less than width "A." In other examples, width "B" may be substantially greater than width "A." Further, it is contemplated that the width of one or more of reinforcement members 38 may taper in any direction along spine member 48. As illustrated in FIG. 7, the width of reinforcement members 38 may taper from width "A" to a width "B," whereby width "B" remains substantially constant in at least a portion of the distal region 26 of introducer 10. Additionally, it can be appreciated that any example spine member described herein may include a given wall thickness at various locations along its length. It can further be appreciated that the wall thickness of any spine member described herein may vary along its length FIGS. 6 and 7 show spine members 40 and 48 including collar portions 82. Collars 82 may be utilized during the manufacturing process and may or may not be positioned at the distal 26 and/or proximal 24 end of spine members 40 and 48. In some instances, collars 82 may be removed during the manufacturing process.

In some instances, manufacturing introducer 10 may result in introducer 10 having one or more radially extending bumps (e.g., raised portions, ridges, etc.). The raised portions may extend radially away from the outer surface of introducer 10. For example, the one or more raised portions may extend radially away from the outer surface of outer sheath 30. For example, in some examples a raised portion may substantially align with (e.g., be positioned above) a folded portion 34 of liner 20.

Figure 8:
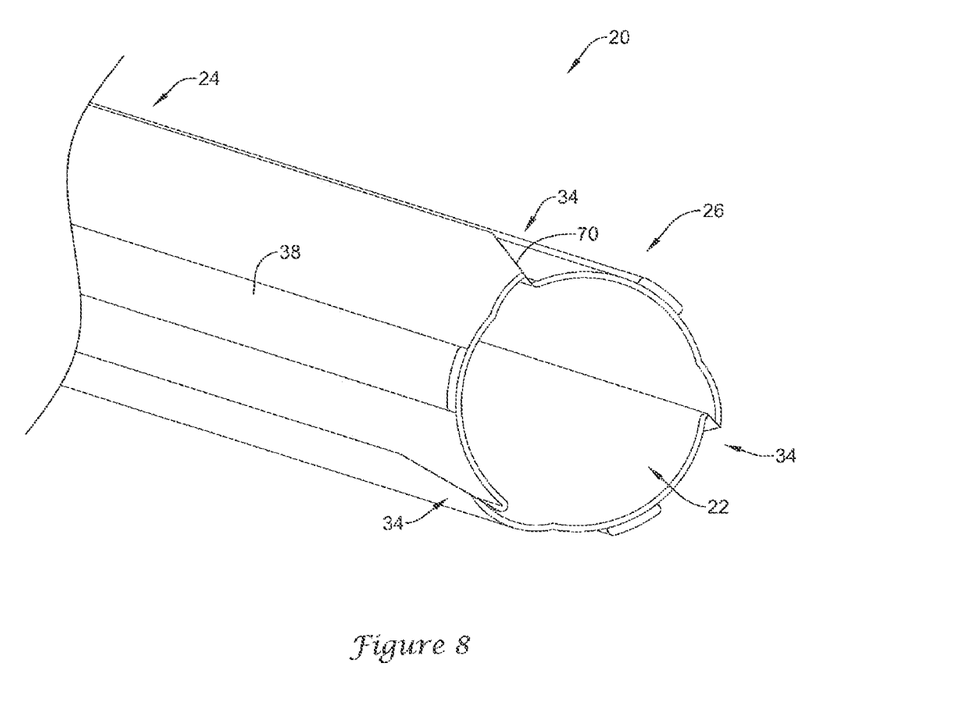
FIG. 8 is a perspective view of an example introducer.

In some instances it may be desirable to remove at least a portion of raised portion prior to performing one or more manufacturing steps (e.g., adding a tip member). FIG. 8 illustrates an example section of liner 20 which may be removed prior to performing one or more manufacturing steps. For example, FIG. 8 shows a line 70 along which a cut, skive, grinding, shaving, etc. may be performed to remove material prior to performing one or more manufacturing steps. It can appreciated that any suitable method may be utilized to remove a portion of liner 20.

In some examples, the material removed from liner 20 may include a portion of one or more folded sections 34. For example, FIG. 8 shows line 70 which may represent a cut which removed a portion of folded section 34. Additionally, FIG. 8 shows reinforcement members 38. Reinforcement members 38 may have material removed from a distal end thereof. For example, one or more reinforcement members 38 may include a tapered, beveled or chamfered distal end.

Figure 9:
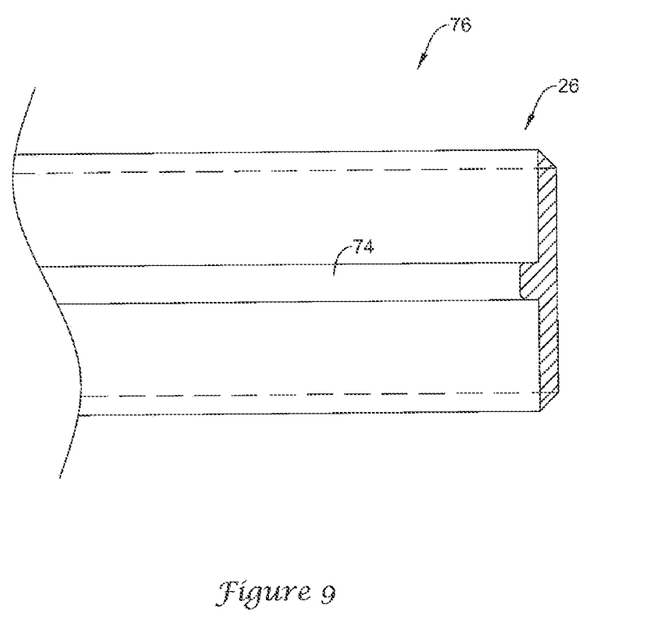
FIG. 9 is a side view of an example introducer.

Additionally, in some examples the distal end of the liner 20, sheath 30 and/or spine 40 may have material uniformly removed prior to performing additional manufacturing steps (e.g., adding a tip member). FIG. 9 shows a general illustration of the end of liner 20, which may or may not include outer sheath 30 and/or reinforcement members 38. For example, reference number 76 may define a liner 20, outer sheath 30, spine 40 or any combination thereof. Additionally, reference numeral 74 may define a spine member or folded section 34 of liner 20.

As shown in FIG. 9, the distal end 26 of example member 76 may include a radius, chamfer and/or bevel around the circumference example member 76. This bevel, chamfer and/or radius may represent material which has been removed from the distal end of example member 76 prior to performing additional manufacturing steps. Additionally, it is contemplated that in some examples, the liner/spine 20/40 discussed in FIG. 4 may have a bevel, chamfer and/or radius applied to its distal end during the manufacturing process.

Figure 10:
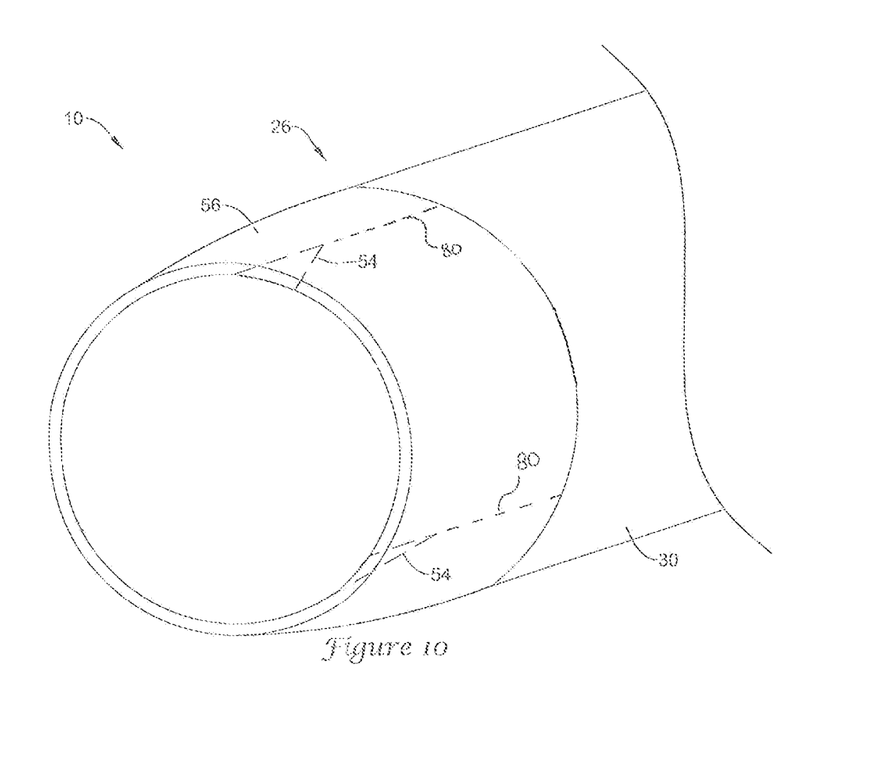
FIG. 10 is a perspective view of an example introducer including tip member.

In some examples it may be desirable to add a tip member to the distal end of any of the examples disclosed herein. FIG. 10 shows an example tip member 56 disposed along the distal region 26. Tip member 56 may be designed with a low durometer material. In some instances, a lower durometer material may provide tip member 56 with the ability to radially expand (e.g., flex) outward and radially contract as a variety of medical devices are advanced through tip member 56. Further, tip member 56 may include a taper. As shown in FIG. 10, tip member 56 may taper from a first diameter in which it contacts outer sheath 30 to a second diameter at the distal end of introducer 10. While not intended to be limiting, in some examples the shape of tip member 56 may resemble a bull-nose.

Additionally, tip member 56 may include a radiopaque material. The radiopaque material may allow tip member 56 to be visualized by a clinician during a medical procedure. Additionally, FIG. 10 shows the portion 54 of fold 34 which had been removed (as discussed with respect to FIG. 8) prior to the application of tip member 56. In some instances, portion 54 may correspond to a portion of fold 34 which had been cut off prior to application of tip member 56. In some examples, tip member 56 may include one or more preferential tear regions 80. Tear regions 80 may be defined as a slit, score, skive, groove, etc. which may preferentially tear upon radially expansion of tip member 56.

In some examples, the example expandable introducer 10 may be disposed about or inserted over a guidewire (not shown), although the guidewire is not required. In some examples, the expandable introducer 10 and/or liner 20 may include a proximal non-expandable section and a distal expandable section. In examples having a proximal non-expandable section, the proximal non-expandable section may have an inner diameter or extent sufficient to accept a medical device passing therethrough, while the distal expandable section may have an inner diameter or radial extent in a relaxed condition that is less than a maximum outer diameter or extent of the medical device. The expandable introducer 10 and/or liner 20 may be formed using any of the techniques or structures discussed herein.

A method of use of introducer 10 may include inserting introducer 10 into and/or navigated within a vessel or body lumen to a target site or area of interest. In some embodiments, the vessel or body lumen may include a partial or total occlusion or obstruction formed therein. Importantly, the introducer 10 may be used in a vessel or body lumen that does not include a partial or total occlusion therein.

After navigating the introducer 10 to the target site or area of interest, an elongate dilator may be inserted into the lumen 22 of the liner 20 and advanced distally toward the distal end 26 of introducer 10, liner 20, and/or outer sheath 30. As the dilator reaches, encounters, and/or engages the lumen 22 of the liner 20, the dilator may exert a radially outward force from within the lumen 22 upon the wall of the liner 20 and/or the outer sheath 30. The radially outward force may cause the outer sheath 30 to separate, split, or tear along and/or through the plurality of openings, cutouts, perforations, notches, holes, apertures, or other weakening features formed in the wall of the outer sheath 30 as the dilator is advanced distally through the lumen 22 of the liner 20. As the outer sheath 30 separates, splits, or tears apart, the one or more folds 34 of the liner 20 are permitted to unfold and increase the inner diameter of the lumen 22. In a vessel or body lumen having a partial or total occlusion, when the dilator may be advanced through the occlusion and/or the outer sheath 30 is opened/expanded within the occlusion, the vessel or body lumen may be deformed or distended by the rigidity of the dilator moving the occlusive material radially outward. Once positioned appropriately adjacent the target site, introducer 10 may be utilized as an access pathway for additional medical devices.

In some examples, introducer 10 may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer 10 may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer 10 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An expandable introducer, formed as:
   an outer sheath;
   a compliant inner liner including a lumen and a distal region;
   at least one folded portion extending along the distal region;
   a reinforcing member having a length and including at least one spine extending along the length of the reinforcing member;
   wherein the outer sheath is directly attached to at least a portion of the compliant inner liner, the reinforcing member, or both the compliant inner liner and the reinforcing member, wherein the outer sheath includes at least one perforation;
   wherein material adjacent to the at least one folded portion is removed from a distal region of the compliant inner liner to form a tip region; and
   a tip member disposed along the tip region.

* * * * *